(12) United States Patent
Dowdle et al.

(10) Patent No.: US 11,253,811 B2
(45) Date of Patent: *Feb. 22, 2022

(54) PROCESS FOR REDUCING ENERGY CONSUMPTION IN THE REGENERATION OF HYBRID SOLVENTS

(71) Applicant: Dow Global Technologies LLC, Midland, MI (US)

(72) Inventors: John R. Dowdle, Lake Jackson, TX (US); Christophe R. Laroche, Lake Jackson, TX (US); Diego Ortiz Vega, Houston, TX (US); Linda L. Pirtle, Brazoria, TX (US)

(73) Assignee: Dow Global Technologies LLC, Midland, MI (US)

( * ) Notice: Subject to any disclaimer, the term of this patent is extended or adjusted under 35 U.S.C. 154(b) by 371 days.

This patent is subject to a terminal disclaimer.

(21) Appl. No.: 16/491,905

(22) PCT Filed: Apr. 19, 2017

(86) PCT No.: PCT/US2017/028323
§ 371 (c)(1),
(2) Date: Sep. 6, 2019

(87) PCT Pub. No.: WO2018/164704
PCT Pub. Date: Sep. 13, 2018

(65) Prior Publication Data
US 2021/0138389 A1     May 13, 2021

Related U.S. Application Data

(60) Provisional application No. 62/467,857, filed on Mar. 7, 2017.

(51) Int. Cl.
*B01D 53/00*     (2006.01)
*B01D 53/14*     (2006.01)
(Continued)

(52) U.S. Cl.
CPC ..... *B01D 53/1425* (2013.01); *B01D 53/1468* (2013.01); *B01D 53/1475* (2013.01);
(Continued)

(58) Field of Classification Search
CPC .......... C07C 7/11; C07C 9/04; C07C 51/487; C07C 59/48; C07C 59/64; B01D 53/52;
(Continued)

(56) References Cited

U.S. PATENT DOCUMENTS 4,085,192 A    4/1978  Van Scoy
4,144,039 A    3/1979  Blanc et al.
(Continued)

FOREIGN PATENT DOCUMENTS

WO        86/05474 A1    9/1986
WO    2016/144179 A1    9/2016

OTHER PUBLICATIONS

PCT/US2017/028323, International Search Report and Written Opinion dated Nov. 9, 2017.
(Continued)

*Primary Examiner* — Sharon Pregler

(57) ABSTRACT

Disclosed is a process for regenerating a hybrid solvent used to remove contaminants from a fluid stream and to provide an improved yield of purified fluid. Said process comprises at least one purification unit (12) and at least one regeneration unit (40) wherein condensed water 62 from the regeneration unit is recycled back into the purification unit and none of the condensed water is reintroduced into the regeneration unit.

5 Claims, 2 Drawing Sheets

(51) Int. Cl.
- *B01D 53/52* (2006.01)
- *B01D 53/78* (2006.01)
- *B01D 53/96* (2006.01)
- *C07C 7/11* (2006.01)
- *C07C 7/12* (2006.01)
- *C10L 3/10* (2006.01)

(52) U.S. Cl.
CPC ....... *B01D 53/1493* (2013.01); *B01D 53/526* (2013.01); *B01D 53/78* (2013.01); *B01D 53/96* (2013.01); *C07C 7/11* (2013.01); *C07C 7/12* (2013.01); *C10L 3/103* (2013.01); *C10L 3/104* (2013.01); *B01D 2252/103* (2013.01); *B01D 2252/2026* (2013.01); *B01D 2252/20489* (2013.01); *B01D 2252/504* (2013.01); *B01D 2257/304* (2013.01); *B01D 2257/504* (2013.01); *C10L 2290/541* (2013.01); *C10L 2290/542* (2013.01)

(58) Field of Classification Search
CPC ...... B01D 53/14; B01D 53/18; B01D 53/265; B01D 53/343; B01D 53/96
See application file for complete search history.

(56) References Cited

U.S. PATENT DOCUMENTS

| | | |
|---|---|---|
| 4,372,925 A | 2/1983 | Cornelisse |
| 4,452,763 A | 6/1984 | van de Kraats et al. |
| 4,545,965 A | 10/1985 | Gazzi et al. |
| 5,716,587 A | 2/1998 | Khanmamedov |
| 6,071,484 A | 6/2000 | Dingman, Jr. et al. |
| 6,203,599 B1 | 3/2001 | Schubert et al. |
| 7,824,542 B2 | 11/2010 | Menzel |
| 2016/0001223 A1 | 1/2016 | Okuno et al. |
| 2018/0272269 A1* | 9/2018 | Goetheer ........... B01D 53/1468 |

OTHER PUBLICATIONS

PCT/US2017/028323, International Preliminary Report on Patentability dated Sep. 19, 2019.

* cited by examiner

PROCESS FOR REDUCING ENERGY CONSUMPTION IN THE REGENERATION OF HYBRID SOLVENTS

FIELD OF THE INVENTION

The present invention relates to a process for regenerating a hybrid solvent used to remove contaminants from a fluid stream and improving the yield of the resulting purified stream. Preferably, said fluid stream is a natural gas stream.

BACKGROUND OF THE INVENTION

Fluid streams derived from natural gas reservoirs, petroleum or coal, often contain a significant amount of acid gases, for example carbon dioxide, hydrogen sulfide, sulfur dioxide, carbon disulfide, carbonyl sulfide, hydrogen cyanide, ammonia, or mercaptans as impurities. Said fluid streams may be gas, liquid, or mixtures thereof, for example gases such as natural gas, refinery gas, hydrocarbon gases from shale pyrolysis, synthesis gas, and the like or liquids such as liquefied petroleum gas (LPG) and natural gas liquids (NGL). Various compositions and processes for removal of acid gas contaminants are known and described in the literature.

Acid gas removal from gas streams, particularly removal of hydrogen sulfide and carbon dioxide from gas streams formed in refinery process units, synthesis gas production plants and oil and gas production facilities, is necessary to allow this gas to be used and/or sold into pipeline systems. The removal of sulfur compounds from these acid gases or "sour gases" is called "sweetening."

Typically, acid gases are removed using a solvent to remove the acid gas via the production of a rich solvent. For example, it is well-known to treat such fluid streams with chemical solvents, physical solvents, or combinations thereof. Chemical solvents such as amine solutions rely on a chemical reaction between the solvent and acid gas contaminants. The amine usually contacts the acidic gas contaminants in the fluid stream as an aqueous solution containing the amine in an absorber tower with the aqueous amine solution contacting the fluid stream counter currently. The regeneration of chemical solvents is achieved by the application of heat.

Alternatively, fluid streams may be treated with physical solvents, such as refrigerated methanol, dialkyl ethers of polyethylene glycols (DEPG), N-methyl-2-pyrrolidones (NMP), propylene carbonate, and the like which do not react chemically with the acid gas impurities. Physical solvents dissolve (absorb) the acid gas contaminants from the fluid stream, typically under high pressure. Since no chemical reactions are involved, physical solvent processes usually require less energy than chemical solvent processes. While the regeneration of chemical solvents is achieved by the application of heat, physical solvents can be stripped of impurities by reducing the pressure without the application of heat. Physical solvents tend to be favored over chemical solvents when the partial pressures of acid gases or other impurities are very high. Unlike chemical solvents, physical solvents are non-corrosive, requiring only carbon steel construction.

Acid gas contaminants are removed by contacting the contaminated product gas with fresh solvent in an absorber or other specialized equipment operated under conditions of high pressure and/or low temperature which are favorable for the type of solvent used. Once the contaminants are removed, the decontaminated gas is ready for sale, for use, or for additional downstream conditioning, depending on the product stream specifications. The solvent is regenerated for reuse by driving off the absorbed contaminants under low pressure and/or high temperature conditions favorable for desorption. Flash tanks and/or stripper columns are typically used to effect this separation.

While numerous prior art processes and systems for acid gas absorption and solvent regeneration are known in the art, many suffer from one or more disadvantage or inefficiency. There is an ever-existing desire to further improve these technologies, e.g., in respect of purification and energy consumption.

SUMMARY OF THE INVENTION

An object of the present invention is to improve conventional solvent regeneration technology for use in processing fluid streams.

In one embodiment the present invention is a process for treating a hydrocarbon fluid stream containing one or more acid gas, preferably the fluid stream is derived from natural gas and is a gas, a liquid, or mixtures thereof comprising the steps of: i) absorbing one or more acid gas from the hydrocarbon fluid stream in a first purification unit by counter currently contacting the fluid stream with a lean hybrid solvent comprising a chemical solvent, preferably is monoethanolamine, methylethanolamine, monoisopropanolamine, diisopropanolamine, 2-hydroxyethylpiperazine, piperazine, 1-methylpiperazine, 2-methylpiperazine, 2-(2-aminoethoxy) ethanol; 2-(2-tertiarybutylamino)propoxyethanol, 2-(2-tertiarybutylamino)ethoxyethanol, 2-(2-isopropylamino)propoxyethanol, tertiaryamylaminoethoxyethanol, (1-methyl-2-ethylpropylamino)ethoxyethanol; tris(2-hydroxyethyl)amine (triethanolamine, TEA); tris(2-hydroxypropyl)amine (triisopropanol); tributanolamine; bis(2-hydroxyethyl)methylamine (methyldiethanolamine, MDEA); 2-diethylaminoethanol (diethylethanolamine, DEEA); 2-dimethylaminoethanol (dimethylethanolamine, DMEA); 3-dimethylamino-1-propanol; 3-diethylamino-1-propanol; 2-diisopropylaminoethanol (DIEA); N,N'-bis(2-hydroxypropyl)methylamine (methyldiisopropanolamine, MDIPA); N,N'-bis(2-hydroxyethyl)piperazine (dihydroxyethylpiperazine, DiHEP)); diethanolamine (DEA); 2-(tert-butylamino)ethanol; 2-(tert-butylaminoethoxy)ethanol; 1-amino-2-methylpropan-2-ol; 2-amino-2-methyl-1-propanol (AMP), 2-(2-aminoethoxy) ethanol, and blends thereof; a physical solvent, preferably the physical solvent is dimethyl ether of polyethylene glycol; propylene carbonate; N-methyl-2-pyrrolidone; methanol; N-acetylmorpholine; N-formylmorpholine; 1,3-dimethyl-3,4,5,6-tetrahydro-2(1H)-pyrimidinone; methoxytriglycol; glycerol; sulfolane; ethylene glycol; or blends thereof; and water, preferably from 5 to 40 weight percent water based on the total weight of the hybrid solvent, to produce a purified hydrocarbon fluid stream and a rich hybrid solvent containing hybrid solvent, hydrocarbons, and acid gas(es); ii) passing the rich hybrid solvent to a separation unit to separate hydrocarbons from the rich hybrid solvent providing a hydrocarbon stream and a rich hybrid solvent stream containing acid gas(es) having a low hydrocarbon content; iii) passing the rich hybrid solvent stream containing acid gas(es) with low hydrocarbon content to a regenerating unit to produce a gas stream comprising acid gas(es), water vapor, and residual hybrid solvent and a regenerated lean hybrid solvent stream; iv) condensing the gas stream to provide an acid gas stream and a water stream comprising residual acid gases and/or hybrid solvent; and v)

recycling all or a portion of the water stream back into the purification unit, wherein no portion of said water stream produced in step iv) is introduced back into the regenerating unit.

DETAILED DESCRIPTION OF THE INVENTION

Figure 1:
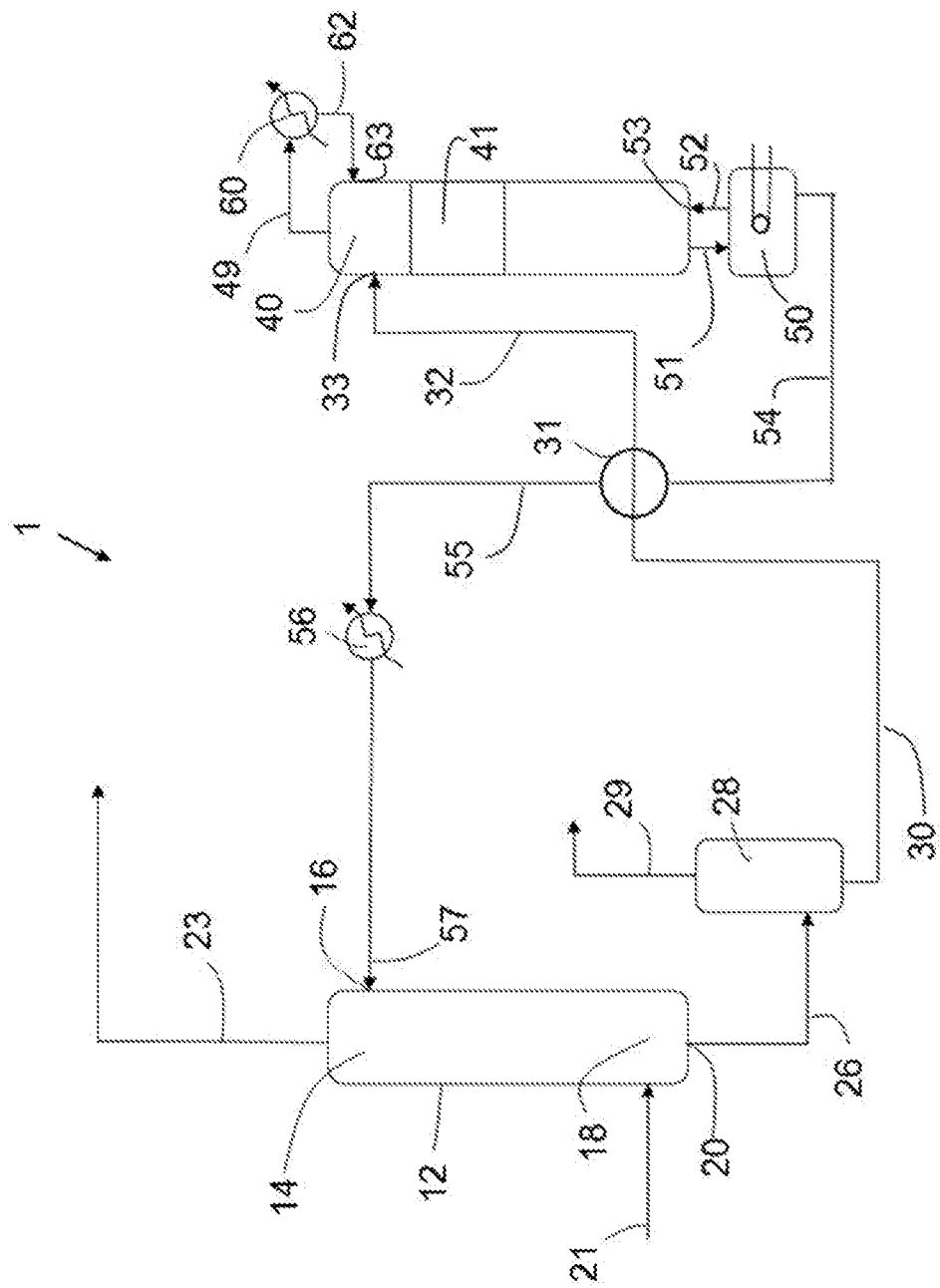
FIG. 1 is a schematic of a process for treating a fluid stream comprising a regeneration stage of a known configuration.

The invention relates to treatment of fluids to remove acid gases, in which the fluid stream is contacted with a hybrid solvent which preferentially absorbs the acid gases. More particularly, the invention is concerned with the regeneration of a hybrid solvent of the type specified for reuse and maximizing the amount of purified fluid stream produced.

Fluid streams treatable by the process of the present invention may be a gas, a liquid, or mixtures thereof, for example gases produced by a gasifier comprising hydrogen, carbon dioxide, and carbon monoxide; a syngas stream comprising hydrogen, carbon dioxide, and carbon monoxide; natural gas; refinery gas; hydrocarbon gases from shale pyrolysis; synthesis gas; and liquids such as liquefied petroleum gas (LPG) and natural gas liquids (NGL). For example, fluid streams derived from natural gas reservoirs, petroleum, or coal, comprise methane ($CH_3$) and commonly exist in mixtures with other hydrocarbons, principally ethane ($C_2H_6$), propane ($C_3H_8$), butanes ($C_4H_{10}$), pentanes ($C_5H_{12}$), and to a lesser extent, heavier hydrocarbons. Such fluid streams comprise a variety of impurities such as hydrogen ($H_2$), water ($H_2O$), carbon monoxide (CO), nitrogen ($N_2$), and acid gases, for example carbon dioxide ($CO_2$), hydrogen sulfide ($H_2S$), sulfur dioxide ($SO_2$), carbon disulfide ($CS_2$), ammonia ($NH_3$), hydrogen cyanide (HCN), carbonyl sulfide (COS), and/or mercaptans. In one embodiment, the term "contaminant" refers generally to one or more of $C_2$ or heavier hydrocarbons, impurities, acid gases, and mixtures thereof to be removed from a fluid stream.

The term "hybrid solvent", as used herein, shall mean a solution comprising a combined chemical solvent and physical solvent with some water, which solutions are capable of absorbing acid gases. Suitable hybrid solvents useful in the process of the present invention may remove one or more of the above listed contaminants from the fluid stream. Solvents may be non-selective, i.e., remove one or more heavier hydrocarbon/impurity/acid gas or selective, i.e., they may target specific heavier hydrocarbons/impurities/acid gas(es).

Preferably, the chemical solvent is one or more amino compound. Suitable amino compounds may be selected from a primary amine, a secondary amine, a tertiary amine, or blends thereof. Alkanolamines are suitable, especially those having 1 to 4 and preferably 2 to 3 carbon atoms per alkanol radical, while dialkanolamines are particularly advantageous. Amino compounds useful in the process of the present invention include, but are not limited to, monoethanolamine, methylethanolamine, monoisopropanolamine, diisopropanolamine, 2-hydroxyethylpiperazine, piperazine, 1-methylpiperazine, 2-methylpiperazine, 2-(2-aminoethoxy) ethanol; 2-(2-tertiarybutylamino)propoxyethanol, 2-(2-tertiarybutylamino)ethoxyethanol, 2-(2-isopropylamino)propoxyethanol, tertiaryamylaminoethoxyethanol, (1-methyl-2-ethylpropylamino)ethoxyethanol; tris(2-hydroxyethyl)amine (triethanolamine, TEA); tris(2-hydroxypropyl)amine (triisopropanol); tributanolamine; bis(2-hydroxyethyl)methylamine (methyldiethanolamine, MDEA); 2-diethylaminoethanol (diethylethanolamine, DEEA); 2-dimethylaminoethanol (dimethylethanolamine, DMEA); 3-dimethylamino-1-propanol; 3-diethylamino-1-propanol; 2-diisopropylaminoethanol (DIEA); N,N'-bis(2-hydroxypropyl)methylamine (methyldiisopropanolamine, MDIPA); N,N'-bis(2-hydroxyethyl)piperazine (dihydroxyethylpiperazine, DiHEP)); diethanolamine (DEA); 2-(tert-butylamino)ethanol; 2-(tert-butylaminoethoxy)ethanol; 1-amino-2-methylpropan-2-ol; 2-amino-2-methyl-1-propanol (AMP), 2-(2-aminoethoxy) ethanol, and blends thereof.

A hybrid solvent suitable for use in the present invention comprises a chemical solvent in an amount of equal to or less than 70 weight percent, preferably equal to or less than 60 weight percent, more preferably equal to or less than 50, and more preferably equal to or less than 40 weight percent weight percent based on the total weight of the hybrid solvent. Preferably the amount of the chemical solvent present in the hybrid solvent is an amount of equal to or greater than 5 weight percent, more preferably equal to or greater than 10 weight percent, more preferably equal to or greater than 20, and preferably equal to or greater than 30 weight percent based on the total weight of the hybrid solvent.

Suitable physical solvents include, but are not limited to, one or more of dimethyl ether of polyethylene glycol (DMPEG), propylene carbonate (PC), N-methyl-2-pyrrolidone (NMP), methanol (MeOH), blends of N-acetylmorpholine and N-formylmorpholine, 1,3-dimethyl-3,4,5,6-tetrahydro-2(1H)-pyrimidinone (DMTP), methoxytriglycol (MTG), glycerol, sulfolane, ethylene glycol, and blends thereof.

DMPEG is a mixture of dimethyl ethers of polyethylene glycol ($CH_3O(C_2H_4O)_nCH_3$ (n is from 2 to 9) used in what is referred to as the SELEXOL™ process to physically absorb $H_2S$, $CO_2$, and mercaptans from gas streams, for example see U.S. Pat. No. 6,203,599 which is incorporated herein in its entirety. Solvents containing DMPEG are licensed and/or manufactured by several companies including Coastal Chemical Company (as COASTAL™ AGR) and Dow (SELEXOL). Other process suppliers such as Clariant GmbH of Germany offer similar solvents. Clariant solvents are a family of dialkyl ethers of polyethylene glycol under the GENOSORB™. DMPEG can be used for selective $H_2S$ removal which requires stripping, vacuum stripping, or a reboiler.

A hybrid solvent suitable for use in the present invention comprises a physical solvent in an amount of equal to or less than 70 weight percent, preferably equal to or less than 60 weight percent, more preferably equal to or less than 50, and more preferably equal to or less than 40 weight percent based on the total weight of the hybrid solvent. Preferably the amount of the physical solvent present in the hybrid solvent is an amount of equal to or greater than 5 weight percent, more preferably equal to or greater than 10 weight percent more preferably equal to or greater than 15 weight percent, and more preferably equal to or greater than 25 weight percent based on the total weight of the hybrid solvent.

A hybrid solvent suitable for use in the present invention comprises a condensed stripping solvent, preferably water, that when heated the condensed stripping solvent vaporizes to become a condensable stripping gas, in the case for water it becomes steam. Preferably the amount of condensed stripping gas (in liquid form) is present in the solvent in an amount of equal to or less than 50 weight percent, preferably equal to or less than 40 weight percent, more preferably equal to or less than 30 weight percent based on the total weight of the hybrid solvent. Preferably the amount of condensed stripping gas (in liquid form) is present in the solvent in an amount of equal to or greater than 5 weight percent, more preferably equal to or greater than 15 weight percent and more preferably equal to or greater than 25 weight percent based on the total weight of the hybrid solvent.

A conventional solvent process for removing contaminants from a fluid stream is shown in FIG. 1; the solvent regeneration takes place in a regeneration unit, typically a stripper column with a reboiler at the bottom to furnish heat to the solvent. The stripper column is generally a tower designed to create efficient gas/liquid contact containing either trays or packing. The rich hybrid solvent containing the contaminants, for example sour gases (such as $CO_2$ and $H_2S$) is injected into the stripper column typically at or near a location near the top and flows down the tower while a vaporized condensable stripping gas, for example steam, generated in the reboiler flows up the tower countercurrent to the descending rich solvent. The condensable stripping gas aids in "stripping" the contaminants from the rich hybrid solvent liquid and sends them back up the tower and out the top of the stripper column. The heat added to the stripper reboiler increases the temperature of the hybrid solvent somewhat, but most of the heat goes into vaporizing the condensable stripping gas which, in turn, flows into and up the stripper column. This heat added or inputted into the reboiler must be furnished from an outside source such as steam from another process, heat transfer media circulated through the reboiler, or directly fired into the reboiler. When contaminants, as gas and/or vapor, pass out the top of the stripper column, a large amount of condensable stripping gas also goes out as an admixture with the contaminants. This overhead condensable stripping gas and gas/vapor stream (called overhead) can be higher in temperature than the feed to the top of the stripper column. The gases and condensable stripping gas which flow from the top of the stripper flow to a condenser (called a reflux condenser) where the contaminants are cooled to near ambient temperatures and most of the condensable stripping gas condenses into a condensed stripper gas, for example water. In the traditional solvent unit, this condensed stripper gas is separated via the reflux receiver and is returned near the top of the stripper. Depending on the make-up of the contaminant gases/vapors they may be disposed of, separated, captured, and/or further treated.

FIG. 1 illustrates a conventional fluid stream treatment process including a single purification unit 12 in which a solvent is used to contact and purify the contaminated fluid. In other modes of practice, the purification stage may include a plurality of treatments units in which this purifying action takes place. The multiple units may be the same or different. In other embodiments, membranes may be used in addition to absorbing units and/or as an alternative to scrubbing units.

In many instances, the contact between the solvent and the contaminated fluid, such as a hydrocarbon fluid stream, occurs in unit 12 in counter-current fashion as shown in FIG. 1. The lean solvent enters the first purification unit 12 at an upper end 14 via inlet 16. After having absorbed contaminants from the fluid being treated, the resultant rich solvent exits the first purification unit 12 at a lower end 18 via an outlet 20. The contaminated fluid moves through unit 12 in the opposite direction. Via pathway 21, the contaminated fluid stream enters the first purification unit 12 at lower end 18 and exits in more pure form from upper end 14 via pathway 23. When the purified fluid is a gas, the purified gas might entrain vaporized solvent, water vapor, or the like. It may be desirable to separate the purified gas from such entrained components. Consequently, the purified gas may be directed to an optional condenser (not illustrated in the figure), where the vaporized solvent or water vapor exiting the unit 12 is condensed.

As used herein, the term "lean" with respect to a solvent shall mean that the concentration of contaminants in the solvent is sufficiently low such that mass transfer of contaminant from the fluid being treated to the solvent will occur when the solvent and contaminated fluid are contacted. In one embodiment, a lean solvent includes a regenerated hybrid solvent solution that has been treated to remove contaminant content from a rich hybrid solvent solution, optionally fresh solvent introduced to the system that has not yet been used for purification, and/or a combination of these. In another embodiment, a lean solvent includes a regenerated solvent that has been treated to remove contaminant content from a rich solvent, optionally fresh solvent introduced to the system that has not yet been used for purification, and/or a combination of these. "Fresh solvent" shall refer to a solvent that is being introduced into the treatment system 1 for the first time from a suitable source. Fresh solvent also is lean with respect to contaminants. The term "rich" with respect to a solvent shall refer to a solvent that has picked up contaminants relative to the lean solvent during the course of a purification treatment.

After the rich solvent comprising rich hybrid solvent, low levels of acid gas(es), and low levels of hydrocarbons exits the first purification unit 12, it is desirable to regenerate the solvent so that the solvent can be recycled back to the first purification unit 12 for more cycle(s) of treatment. Accordingly, a first pathway 26 is used to convey the rich solvent to a separation unit, preferably a flash tank 28, where depressurization takes place, thereby desorbing a major part of the absorbed hydrocarbons 29. The rich solvent with lower hydrocarbon content and low levels of acid gas(es) is passed from the flash tank 28 via line 30 through a heat exchanger 31 and line 32 then introduced into the top of a regeneration column, preferably a stripper column 40 where the lean solvent is regenerated from the rich solvent. For purposes of illustration, FIG. 1 shows a regeneration unit that includes as a stripper column 40 having a top and a bottom and comprising at least one section of vapor-liquid contacting device(s) 41, sometimes referred to as stage(s) and a corresponding reboiler 50. In a traditional stripper column 40 the rich solvent typically enters towards the top of the column at a location 33 which is equal to or lower than the location of the condensed stripper gas return 63 from the reflux receiver 60.

As used herein, and with respect to a column, the terms "upper" and "lower" should be understood as relative to each other. For example, withdrawal or addition of a stream from an upper portion of a column means that the withdrawal or addition is at a higher position (relative to the ground when the column is in operation) than a stream withdrawn or added from a lower region of the same column. Viewed from another perspective, the term upper may thus refer to the upper half of a column, whereas the term lower may refer to the lower half of a column. Similarly, where the term "middle" is used, it is to be understood that a middle portion of the column is intermediate to an upper portion and a lower portion. However, where upper, middle, and lower are used to refer to a column, it should not be understood that such column is strictly divided into thirds by these terms.

In other embodiments of the prior art and the present invention, the stripper column 40 may comprise as many vapor-liquid contacting sections as needed to provide lean solvent, for example as many as 1 to 20 sections or more (2 to 20 section not depicted in FIG. 1), in other words the stripper column may comprise 1, 2, 3, 4, 5, 6, 7, 8, 9, 10, 11, 12, 13, 14, 15, 16, 17, 18, 19, 20, or more sections. Each vapor-liquid contacting section may comprise mass transfer devises, such as packing or trays, to facilitate the desorption of the contaminants.

As used herein, with respect to vapor-liquid contacting sections, the term portion of a section should be understood to mean that there may be a location within the section wherein some part or fraction of the section is above that location and some part or fraction of the section is below that location.

In other modes of practice of the prior art and the present invention, the first portion of the regeneration stage may include a plurality of stripper units with at least two sections and/or reboiler units in which corresponding regeneration action takes place. The multiple units may be the same or different. In addition to the stripper column 40, other kinds of regeneration equipment can be used to help regenerate lean solvent if desired.

As shown in FIG. 1, first pathway 32 is used to convey the rich solvent from the heat exchanger 31 to the upper portion, at or above the first section 41, of stripper column 40 at an inlet position 33. The solvent then is treated in stripper column 40 by contacting the solvent with condensable stripping gas to heat the solvent. Generally, the solubility of dissolved contaminants, such as acid gases, tends to decrease as the temperature of the solvent increases. Thus, heating the solvent with the condensable stripping gas in the stripper column 40 as the solvent moves from the top of the column to the bottom of the column strips away contaminants to provide a solvent that is more lean with respect to these contaminants.

Stripped contaminants exit the top of the stripper column 40 via line 49 with the condensable stripper gas (for example steam) as an admixture of contaminants, steam, possibly solvent, possibly residual hydrocarbons and/or acid gas(es). The admixture is directed to a condenser 60. In condenser 60, solvent, condensed stripper gas (for example condensed water vapor), and other compounds that may leave the top the stripper column 40 together with stripped contaminants are condensed. The stripped contaminants are discharged from the condenser to line 61 for further downstream processing or disposal as desired. At least part of the condensed stripping gas, e.g., water vapor, and/or solvent, and/or low levels of hydrocarbons, and/or residual levels of acid gas(es), and other compounds that may have condensed is returned via line 62 to the upper portion of the stripper column 40 at or above the same location of the rich feed at the return position 63 and is used to aid in stripping the contaminants from the solvent being regenerated.

Solvent leaving the bottom of the stripper column through line 51 passes to a reboiler 50 which is connected back to the stripper column by return line 52 and reenters the stripper column at location 53. The solvent circulating through the reboiler 50 is heated to produce additional steam which is feed back into the stripper column 40. Solvent will have an extended residence time in these units 40 and 50 until a portion of the solvent exits reboiler 50 via line 54 through the heat exchanger 31 and back to the purification unit 12.

The hot solvent leaving reboiler 50 via line 54 heats up the solvent being transported to the stripper column 40 via line 30 in the heat exchanger 31, while the relatively cooler solvent being conveyed to the stripper column 40 in line 31 cools the relatively hot solvent leaving reboiler 50 in line 54. An additional cooling unit 56 may be incorporated into line 55 to further cool the lean solvent prior to the solvent being introduced to the purification unit 12 via inlet 16.

One of the objects of the process of the present invention is to improve the efficiency of the regeneration step, specifically the saving of energy required for regenerating the hybrid solvent. In one embodiment of the process of the present invention FIG. 2, this is accomplished by eliminating the step of recycling the stripping solvent content, i.e., the water stream, back into the regeneration column, preferably a stripper column 40. In the process of the present invention, the water which is condensed in the condenser 60 is not reintroduced into the top of the stripper column 40 as in the conventional fluid stream treatment process. Reducing the water content means that, at the same temperature, the hybrid solvent has a lower total vapor pressure resulting in a lower total pressure for a regeneration step at a fixed temperature. This will cause the partial pressure of the acid component to be further from its equilibrium value and hence the driving force for mass transfer (stripping) to be greater. However, it will usually not be possible to operate the regenerator at lower pressure since this is determined by downstream units. In this case the pressure may be kept the same, and, providing there are no heat transfer constraints, the temperature may be raised. This again is advantageous for the stripping, since at a higher temperature the acid gas is less soluble.

In addition, the reduced proportion of water in the hybrid solvent reduces the strength of the chemical bond between the hybrid solvent and the acid gas, which lowers the resistance of the absorbed gases to stripping For the invention to make a significant effect on the energy consumption required for regeneration of a hybrid solvent, the hybrid solvent should not contain so much water that its removal from the regeneration zone does not substantially alter the thermodynamic and chemical conditions obtaining there. Some water/steam should, nevertheless, remain in the regenerator as this is necessary for the removal of the acid gases from the regenerator. Furthermore, sufficient water should be present in the hybrid solvent that a significant proportion of it can be withdrawn from the regenerator without the temperature at the bottom of the regenerator becoming unstable due to excessively low partial pressure of the remaining water; a remedy for this phenomenon is, however, proposed below.

Figure 2:
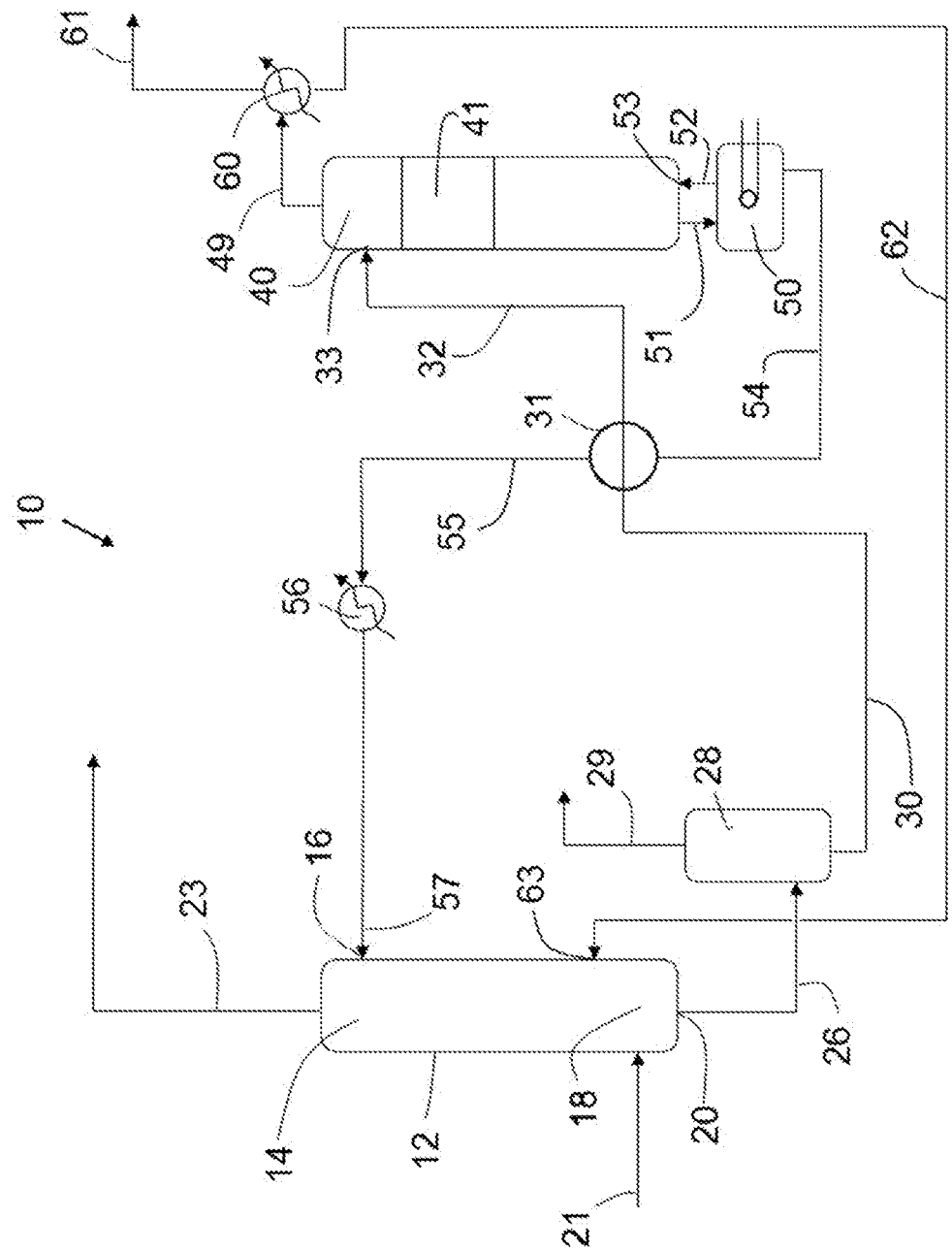
FIG. 2 is a schematic of an embodiment of a process for treating a fluid stream of the present invention.

Referring now to FIG. 2, in the treatment system 10 of the present invention, the stripped contaminants exit the top of the stripper column 40 via line 49 with the condensable stripper gas (for example steam) as an admixture of contaminants (i.e., low levels of hydrocarbons, acid gas(es) e.g., $H_2S$, hybrid solvent, or mixtures thereof). The admixture is directed to a condenser 60. In the condenser 60, hybrid solvent, condensed stripper gas (for example condensed water vapor), and other compounds that may leave the top of the stripper column 40 together with stripped contaminants are condensed forming a water stream comprising water and possibly low levels of hydrocarbons, hybrid solvent, and or acid gas(es). The non-condensed stripped contaminants are discharged from the condenser 60 to line 61 for further downstream processing or disposal as desired.

In a preferred embodiment of the process of the present invention, none of the water stream comprising condensed stripping gas, e.g., water vapor and/or solvent and other compounds that may have condensed in the condenser 60 is returned to the stripper column 40. All or a portion of the water stream from the condenser 60 is fed into the purification unit 12 via line 62 and enters the purification unit 12 at inlet 63. Inlet 63 is preferably lower on the purification unit 12 than the lean regenerated hybrid solvent inlet 16 and above where the entrance point of the contaminated fluid stream 21.

In another embodiment of the process of the present invention (not shown in the figures), a portion of the condensed stripping gas, e.g., water vapor and/or solvent and other compounds that may have condensed in the condenser 60 is returned to the stripper column 40 and the remaining portion of condensed stripping gas is introduced into the purification unit 12 via line 62.

The present invention provides for plant and process to treat a fluid stream which (1) is more energy efficient and/or cost effective by lowering the amount of energy required to produce a lean solvent stream from a rich solvent stream and (2) provides a higher yield of the purified fluid stream.

EXAMPLES

Simulation of a Stripping Column with Condenser Feed Modification.

Two different systems are simulated and compared. In Comparative Example A, a conventional gas treating process is modeled (e.g., as in FIG. 1). In Example 1, a gas treating process of the present invention is modeled (e.g., FIG. 2). The simulations are performed using Aspen Plus software. The property method used for the fluid phases is the electrolyte NRTL model of Chen and coworkers, see Song, Y., Chen, C.-C., 2009, Symmetric Electrolyte Nonrandom Two-Liquid Activity Coefficient Model, Ind. Eng. Chem. Res. 48, 7788-7797. doi:10.1021/ie9004578, Kraats, E. J. van de, Darton, R. C., 1984, Process For Regeneration Of Solvents In Hydrogen Sulfide Removal From Gases, and U.S. Pat. No. 4,452,763. Model parameters are developed from pure component and binary vapor-liquid equilibrium data. The absorption and regeneration columns are simulated using Aspen's RateSep model, which is a rate-based column model. The main absorption column has 28 valve trays and operates at 6920 kPa. The regeneration column has 20 valve trays and operates at 175 kPa. The associated condensing unit (60 in FIG. 1 to FIG. 2) temperature is set to 49° C. The rich solvent is fed to the top tray of the regeneration unit at a temperature of 365 K. In the case of the present invention (FIG. 2), the condensed water vapor 62 is sent to the purification unit 12, where it is fed at the location of the 20$^{th}$ tray out of 28 trays on the tower (numbered from top to bottom). Prior to being fed, the condensed water vapor 62 is optionally passed to a pump to increase its pressure to a pressure slightly above the operating pressure of the main absorption column.

The process conditions and composition for the feed gas is shown in Table 1.

TABLE 1

| CONDITIONS | | |
|---|---|---|
| Flow Rate | kmol/s | 1.29 |
| Temperature | K | 305 |
| Pressure | kPa | 6920 |

TABLE 1-continued

| COMPOSITION | | |
|---|---|---|
| Water | Mole fraction | 0.0008 |
| $CO_2$ | Mole fraction | 0.0555 |
| $H_2S$ | Mole fraction | 0.0393 |
| Methane | Mole fraction | 0.8213 |
| Ethane | Mole fraction | 0.0527 |
| Propane | Mole fraction | 0.0208 |
| Butane | Mole fraction | 0.0093 |
| Methyl mercaptan | ppmv | 119 |
| Ethyl mercaptan | ppmv | 85 |
| Propyl mercaptan | ppmv | 27 |
| n-Butyl mercaptan | ppmv | 25 |

The process conditions and composition for the lean hybrid solvent is shown in Table 2. In Table 2, "MDEA" is methyldiethanolamine, "MTG" is methoxytriglycol, and "Loading" for a given acid gas species is defined as the ratio of the amount of moles of that species in solution to the amount of moles of alkanolamine in solution. "MTG" is methoxytriglycol.

In Table 3, "mercaptan removal" is defined as the molar percentage of mercaptans from the feed gas stream that are not recovered in the purified gas stream. In Comparative Example A and Example 1, this difference is between purified gas stream 23 and the feed gas stream 21 in FIG. 1 and FIG. 2, respectively.

TABLE 2

| CONDITIONS | | |
|---|---|---|
| Flow Rate | kmol/s | 1.22 |
| Temperature | K | 317 |
| Pressure | kPa | 6990 |
| COMPOSITION | | |
| Water | Mass fraction | 0.6846 |
| MDEA | Mass fraction | 0.1892 |
| MTG | Mass fraction | 0.1261 |
| $CO_2$ | Loading | 0.0002 |
| $H_2S$ | Loading | 0.0000 |

In the cases of Comparative Example A and Example 1, the processes are designed for selectively removing sulfur, and therefore it is desired to maximize $CO_2$ slip while removing as much of the sulfur-containing compounds as possible. In the case of Comparative Example A, and Example 1, "Product gas" refers to purified gas stream 23 in FIG. 1 and FIG. 2, respectively.

As shown in Table 3, the simulation of the present invention, Example 1, performed significantly better than the traditional simulation, Comparative Example A. There is a 22% percent reduction in the amount of energy required by the reboiler to achieve the same lean loading, and a 24% reduction in total duty with only a slight decrease in mercaptan removal.

TABLE 3

| | | Com. Ex. A | Example 1 |
|---|---|---|---|
| Total Mercaptan Removal | mol % | 89 | 86 |
| $CO_2$ Slip | mol % | 36 | 38 |
| $CO_2$ Concentration in Product Gas | mol % | 2.2 | 2.3 |
| $H_2S$ Concentration in Product Gas | ppmv | 8.4 | 10.1 |
| Total Mercaptan Concentration in Product Gas | ppmv | 29 | 36 |
| Reboiler Duty | GJ/hr | 45 | 35 |
| Total Duty | GJ/hr | 85 | 65 |

What is claimed is:

1. A process for treating a hydrocarbon fluid stream containing one or more acid gas comprising the steps of:
   i) absorbing one or more acid gas from the hydrocarbon fluid stream in a purification unit by counter currently contacting the fluid stream with a lean hybrid solvent comprising a chemical solvent, a physical solvent, and water to produce a purified hydrocarbon fluid stream and a rich hybrid solvent comprising hybrid solvent, hydrocarbons, and acid gas(es);
   ii) passing the rich hybrid solvent to a separation unit to separate hydrocarbons from the rich hybrid solvent providing a hydrocarbon stream and a rich hybrid solvent stream containing acid gas(es) having a low hydrocarbon content;
   iii) passing the rich hybrid solvent stream containing acid gas(es) with low hydrocarbon content to a regenerating unit to produce a gas stream comprising acid gas(es), water vapor, and residual hybrid solvent and a regenerated lean hybrid solvent stream;
   iv) condensing the gas stream to provide an acid gas stream and a water stream comprising residual acid gases and/or hybrid solvent; and
   v) recycling all or a portion of the water stream back into the purification unit, wherein no portion of said water stream produced in step iv) is introduced back into the regenerating unit.

2. The process of claim 1 wherein the fluid stream is derived from natural gas and is a gas, a liquid, or mixtures thereof.

3. The process of claim 1 wherein the physical solvent is dimethyl ether of polyethylene glycol; propylene carbonate; N-methyl-2-pyrrolidone; methanol; N-acetylmorpholine; N-formylmorpholine; 1,3-dimethyl-3,4,5,6-tetrahydro-2(1H)-pyrimidinone; methoxytriglycol; glycerol; sulfolane; ethylene glycol; or blends thereof.

4. The process of claim 1 wherein the chemical solvent is monoethanolamine, methylethanolamine, monoisopropanolamine, diisopropanolamine, 2-hydroxyethylpiperazine, piperazine, 1-methylpiperazine, 2-methylpiperazine, 2-(2-aminoethoxy) ethanol; 2-(2-tertiarybutylamino)propoxyethanol, 2-(2-tertiarybutylamino)ethoxyethanol, 2-(2-isopropylamino)propoxyethanol, tertiaryamylaminoethoxyethanol, (1-methyl-2-ethylpropylamino)ethoxyethanol; tris(2-hydroxyethyl)amine (triethanolamine, TEA); tris(2-hydroxypropyl)amine (triisopropanol); tributanolamine; bis(2-hydroxyethyl)methylamine (methyldiethanolamine, MDEA); 2-diethylaminoethanol (diethylethanolamine, DEEA); 2-dimethylaminoethanol (dimethylethanolamine, DMEA); 3-dimethylamino-1-propanol; 3-diethylamino-1-propanol; 2-diisopropylaminoethanol (DIEA); N,N'-bis(2-hydroxypropyl)methylamine (methyldiisopropanolamine, MDIPA); N,N'-bis(2-hydroxyethyl)piperazine (dihydroxyethylpiperazine, DiHEP)); diethanolamine (DEA); 2-(tert-butylamino)ethanol; 2-(tert-butylaminoethoxy)ethanol; 1-amino-2-methylpropan-2-ol; 2-amino-2-methyl-1-propanol (AMP), 2-(2-aminoethoxy) ethanol, and blends thereof.

5. The process of claim 1 wherein the hybrid solvent comprises 5 to 40 weight percent water based on the total weight of the hybrid solvent.

* * * * *